United States Patent [19]

Meyer et al.

[11] Patent Number: 4,898,877
[45] Date of Patent: Feb. 6, 1990

[54] CIRCULATION-ACTIVE CYCLOHEXENECARBOXYLATES

[75] Inventors: Horst Meyer, West Haven, Conn.; Eckhard Schwenner; Martin Bechem, both of Wuppertal, Fed. Rep. of Germany; Rainer Gross, Wuppertal, Fed. Rep. of Germany; Matthias Schramm, Cologne, Fed. Rep. of Germany; Michael Kayser, Hagen, Fed. Rep. of Germany; Siegbert Hebisch, Oberhausen, Fed. Rep. of Germany

[73] Assignee: Bayer Aktiengesellschaft, Leverkusen, Fed. Rep. of Germany

[21] Appl. No.: 157,678

[22] Filed: Feb. 18, 1988

[30] Foreign Application Priority Data

Mar. 4, 1987 [DE] Fed. Rep. of Germany ....... 3706877

[51] Int. Cl.$^4$ ................. A61K 31/275; A61K 31/215; C07C 121/48; C07C 121/75
[52] U.S. Cl. ..................................... 514/521; 514/522; 514/533; 558/414; 558/426; 560/9; 560/11; 560/12; 560/13; 560/21; 560/45; 560/53; 560/59
[58] Field of Search .................. 558/426, 414; 560/53, 560/59, 21, 45; 514/521, 533, 522

[56] References Cited

FOREIGN PATENT DOCUMENTS 2166019 8/1972 Fed. Rep. of Germany .

OTHER PUBLICATIONS

C.A., 82: 125196t (1975), Brimacombe et al.
C.A., 98: 197983a (1983), Prostakov et al.

*Primary Examiner*—Joseph Paul Brust
*Attorney, Agent, or Firm*—Sprung Horn Kramer & Woods

[57] ABSTRACT

Novel circulation-active cyclohexenecarboxylates of the formula

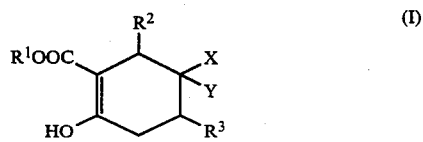

in which
$R^1$ is an organic radical,
$R^2$ is an optionally substituted aryl radical,
$R^3$ is an optionally substituted alkyl or aryl radical,
X and Y are —CN, —COR$^4$, —SO$_2$R$^4$, —COOR$^5$, —CONR$^6$R$^7$ or —SO$_2$NR$^6$R$^7$, and
$R^4$, $R^5$, $R^6$ and $R^7$ are various organic radicals.

12 Claims, No Drawings

CIRCULATION-ACTIVE CYCLOHEXENECARBOXYLATES

The present invention relates to cyclohexenecarboxylates, a process for their preparation and also their use in drugs, in particular in drugs which influence the circulation.

The invention relates to cyclohexenecarboxylates of the general formula (I)

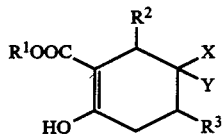

in which $R^1$ represents a straight-chain or branched, or cyclic, saturated or unsaturated hydrocarbon radical with up to 20 carbon atoms, which can be interrupted by an oxygen atom or a sulphur atom in the chain and/or which can be substituted by halogen, cyano, hydroxyl, acetyloxy, nitro, nitrooxy or by a phenyl, phenoxy, phenylthio or phenylsulphonyl group which is optionally substituted by halogen, cyano, dialkylamino with in each case 1 to 2 carbon atoms to each alkyl group, alkoxy with 1 to 4 carbon atoms, alkyl with 1 to 4 carbon atoms, trifluoromethylor nitro, or by an $\alpha$-, $\beta$- or $\gamma$-pyridyl group or by an amino group, where this amino group carries 2 identical or different substituents from the group alkyl with up to 4 carbon atoms, alkoxyalkyl with up to 4 carbon atoms, phenyl or $C_7$–$C_{14}$-aralkyl, or where these substituents optionally form with the nitrogen atom a five- to seven-membered ring, which can contain an oxygen or sulphur atom as an additional hetero atom, or an N-phenyl or N-alkyl grouping, where this alkyl group comprises 1 to 3 carbon atoms, $R^2$ represents $C_6$–$C_{12}$-aryl, which can be mono-, di- or trisubstituted by halogen, $C_1$–$C_8$-alkyl, $C_1$–$C_8$-alkoxy, $C_1$–$C_6$-alkylthio, $C_1$–$C_6$-alkylsulphonyl, trifluoromethyl, trifluoromethoxy, difluoromethoxy, trifluoromethylthio, nitro, cyano, $C_1$–$C_4$-alkoxycarbonyl, di-$C_1$–$C_6$-alkylamino, dimethylaminosulphonyl or dimethylcarbamoyl, the substituents being identical or different, $R^3$ represents $C_1$–$C_6$-alkyl or represents $C_6$–$C_{12}$-aryl, which can be mono- or disubstituted by halogen, $C_1$–$C_4$-alkyl, $C_1$–$C_4$-alkoxy, cyano, trifluoromethyl or trifluoromethoxy, the substituents being identical or different, and X and Y are identical or different and represent a group of the formula —CN, —COR$^4$, —SO$_2$R$^4$, —COOR$^5$, —CONR$^6$R$^7$ or —SO$_2$NR$^6$R$^7$,
wherein
R$^4$ denotes $C_1$–$C_8$-alkyl, $C_6$–$C_{12}$-aryl or $C_7$–$C_{14}$-aralkyl,
R$^5$ denotes $C_1$–$C_8$-alkyl or $C_6$–$C_{12}$-aryl, and
R$^6$ and R$^7$ are identical or different and denote $C_1$–$C_6$-alkyl, $C_6$–$C_{12}$-aryl or $C_7$–$C_{14}$-aralkyl, in the form of their isomers, isomeric mixtures, optical antipodes or racemates.

These compounds of the general formula (I) may preferably be mentioned in which $R^1$ represents a straight-chain or branched, or cyclic, saturated or unsaturated hydrocarbon radical with up to 14 carbon atoms, which can be interrupted by an oxygen atom in the chain and/or can be substituted by fluorine, chlorine, bromine, iodine, cyano, hydroxyl, acetoxy, nitrooxy or by a phenyl or phenoxy group which is optionally substituted by fluorine, chlorine, bromine, alkoxy with 1 to 4 carbon atoms, alkyl with 1 to 4 carbon atoms or trifluoromethyl, or by an $\alpha$-, $\beta$- or $\gamma$-pyridyl group or by an amino group, where this amino group carries 2 identical or different substituents from the group alkyl with 1 to 4 carbon atoms, phenyl or benzyl, $R^2$ represents phenyl or naphthyl, where the radicals mentioned can be mono- or disubstituted by fluorine, chlorine, bromine, $C_1$–$C_6$-alkyl, $C_1$–$C_6$-alkoxy, $C_1$–$C_4$-alkylthio, $C_1$–$C_4$-alkylsulphonyl, trifluoromethyl, trifluoromethoxy, difluoromethoxy, nitro, cyano, $C_1$–$C_4$-alkoxycarbonyl or di-$C_1$–$C_4$alkylamino, the substituents being identical or different, $R^3$ represents $C_1$–$C_4$-alkyl or represents phenyl or naphthyl, where the radicals mentioned can be substituted by fluorine, chlorine, methyl, methoxy or trifluoromethyl and X and Y are identical or different and represent a group of the formula —CN, —COR$^4$, SO$_2$R$^4$, —COOR$^5$, —CONR$^6$R$^7$ or —SO$_2$NR$^6$R$^7$,
wherein
R$^4$ denotes $C_1$–$C_6$-alkyl, phenyl or benzyl,
R$^5$ denotes $C_1$–$C_6$-alkyl or phenyl, and
R$^6$ and R$^7$ are identical or different and denote $C_1$–$C_4$-alkyl, phenyl or benzyl, in the form of their isomers, isomeric mixtures, optical antipodes or racemates.

These compounds of the general formula (I) may particularly preferably be mentioned in which $R^1$ represents a straight-chain or branched or cyclic hydrocarbon radical with up to 8 carbon atoms, which can be interrupted by an oxygen atom in the chain and/or which can be substituted by fluorine, cyano, acetoxy, hydroxyl, phenyl, phenoxy, $\alpha$-, $\beta$- or $\gamma$-pyridyl or an amino group, where this amino group carries two identical or different substituents from the group alkyl with 1 to 2 carbon atoms and benzyl, $R^2$ represents phenyl, which can be mono- or disubstituted by fluorine, chlorine, $C_1$–$C_4$-alkyl, $C_1$–$C_4$-alkoxy, trifluoromethyl or nitro, the substituents being identical or different, $R^3$ represents methyl or phenyl, and X and Y are identical or different and represent a group of the formula —CN, —COR$^4$, —SO$_2$R$^4$ or —COOR$^5$,
wherein
R$^4$ denotes $C_1$–$C_4$-alkyl, phenyl or benzyl and
R$^5$ denotes $C_1$–$C_4$-alkyl, in the form of their isomers, isomeric mixtures, optical antipodes or racemates.

The compounds according to the invention exist in stereoisomeric forms, which either behave as mirror images of each other (enantiomers) or not as mirror images of each other (diastereomers). The invention relates both to the antipodes and also to the racemic forms as well as to diastereomeric mixtures. Like the diastereomers, the racemic forms can be separated into the individual stereoisomeric constituents in a known manner (see E. L. Eliel, Stereochemistry of Carbon Compounds, McGraw Hill, 1962). The cyclohexenecarboxylates of the general formula (I) according to the invention can be obtained when acetoacetic esters of the general formula (II)

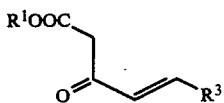

in which

R¹ and R³ have the meaning given above, are reacted with ethenes of the general formula (III)

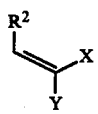

in which

R², X and Y have the meaning given above, in inert solvents, in the presence of bases.

If methyl 3-oxo-5-phenyl-4-pentenoate and benzylidenemalonodinitrile are used as starting substances, then the process according to the invention can be illustrated by the following scheme:

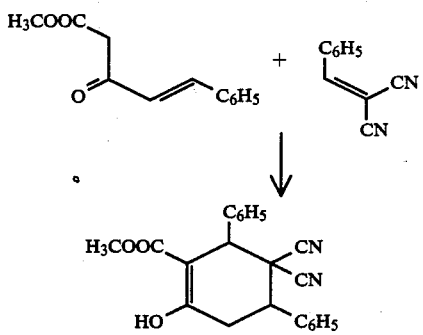

Water and/or organic solvents which are not altered by the reaction conditions are suitable as inert solvents. These preferably include alcohols such as methanol, ethanol, propanol, isopropanol or butanol, or halogenohydrocarbons such as methylene chloride, chloroform, tetrachloromethane, 1,2-dichloroethane or dichloroethylene, or ethers such as diethyl ether, butyl methyl ether, dioxane or tetrahydrofuran, or hydrocarbons such as benzene, toluene or xylene, or amides such as dimethylformamide or hexamethylphosphoric triamide, or ethyl acetate, dimethyl sulphoxide, sulpholane, pyridine, dimethylaminopyridine, picoline, morpholine or piperidine. It is also possible to employ mixtures of the solvents mentioned.

The usual inorganic or organic basic compounds are suitable as bases. These preferably include alkali metal hydroxides or alkaline earth metal hydroxides such as sodium hydroxide, potassium hydroxide or barium hydroxide, or alkali metal carbonates such as sodium carbonate, sodium hydrogen carbonate or potassium carbonate, or alkali metal alcoholates such as sodium methanolate, sodium ethanolate, potassium methanolate, potassium ethanolate or potassium tert-butanolate, or ammonia, or organic amines which are derived from ammonia, such as, for example, triethylamine, diisopropylamine, ethyldiisopropylamine, or organic bases such as pyridine, dimethylaminopyridine, picoline, morpholine, thiomorpholine, piperidine, 1,5-diazabicyclo[4,3,0]non-5-ene (DBN) or 1,5-diazabicyclo[5,4,0]undec-5-ene (DBU).

The reaction is particularly preferably carried out in solvents such as water and/or alcohols such as methanol, ethanol, propanol or isopropanol using aqueous ammonia solution, or alkali metal alcoholates.

The reaction can be carried out at atmospheric pressure, or at increased or decreased pressure. In general, atmospheric pressure is used.

The reaction is generally carried out within a temperature range of 0° C. to +100° C., preferably from +20° C. to +80° C.

In carrying out the reaction the acetoacetic ester is generally employed in an amount of 0.5 to 5, preferably of 1 to 2 mols, based on 1 mol of the ethene. The base is generally employed in an amount of 0.01 to 5 mols preferably of 0.05 to 1 mol, based on 1 mol of the acetoacetic ester.

The reaction is generally carried out by mixing the acetoacetic ester, the ethene and the base in a suitable solvent and heating if necessary. Working-up is performed in the usual manner by extraction, chromatography and/or crystallization.

The acetoacetic esters employed as starting substances are known or can be prepared by known methods, for example from the corresponding aldehydes ($R^3CHO$) with the corresponding phosphoranes ($R_3P=CHCOCH_2COOR^1$) or phosphonates ($(RO_2)_2PO-CH_2COCH_2COOR^1$) by the Wittig or Wittig-Horner reaction [Houben-Weyl's "Methoden der organischen Chemie" ("Methods of Organic Chemistry") V/1b; V/1c; E1; G. Wittig, U. Schöllkopf Org. Synth., Coll. Vol. V, 751 (1973)].

The ethenes of the general formula (III) are known or can be obtained by known methods [Beilstein's Handbuch der organischen Chemie (Beilstein's Handbook of Organic Chemistry) 3- (1), 134; 9, 893].

The compounds according to the invention exhibit an unexpected, valuable pharmacological activity spectrum. They influence the contractility of the heart and the smooth muscle tone. They can therefore be employed in drugs for influencing pathologically altered blood pressure, as coronary therapeutics and for the treatment of coronary insufficiency. Moreover, they can be used for the treatment of arrhythmias, for lowering blood sugar, for detumescence of mucous membranes and for influencing salt and liquid balance.

The cardiac activity has been discovered on isolated guineapig auricles. For this, the left auricles of guineapigs are isolated and hung in a 32° C. thermostated organ bath. A Krebs-Henseleit solution with the following composition (118.5 mmol/l of NaCl, 4.75 mmol/l of KCl, 1.19 mmol/l of $KH_2PO_4$, 119 mmol/l of $MgSO_4$, 25 mmol/l of $NaHCO_3$, 0.013 mmol/l of Na-EDTA, 1.8 mmol/l of $CaCl_2$), with the addition of 10 mmol/l of glucose as an energy liberating substrate, is used as the incubation medium. The solution is treated with Carbogen gas (95% $CO_2$, 5% $O_2$) in order to maintain a pH of 7.4. The left auricles are clamped in the organ bath using a given basal tone, and the tension is recorded by means of a transducer. Using periodical electrical shocks the contractions thus resulting are continuously recorded on a high-speed recorder. In the presence of each of the compounds according to the invention there is a percentage decrease in the contractility relative to the equivalent 100% starting value:

| Example | Concentration (g/l) | % alteration in contractility |
|---|---|---|
| 6 | $10^{-3}$ | −43% |
| 16 | $10^{-3}$ | −27% |
| 18 | $10^{-3}$ | −25% |

The new active compounds can be converted in a known manner into the customary formulations, such as tablets, dragees, pills, granules, aersols and syrups, emulsions, suspensions and solutions, using inert non-toxic, pharmaceutically suitable excipients or solvents. The therapeutically active compound should in each case be present in a concentration of about 0.5 to 90% by weight of the total mixture, that is to say in amounts which suffice to achieve the dosage range indicated.

The formulations are prepared, for example, by extending the active compounds with solvents and/or excipients, where appropriate with the use of emulsifiers and/or dispersing agents, and, for example when using water as a diluent, organic solvents can be used as auxiliary solvents where appropriate.

Examples of auxiliary substances which may be mentioned are: water, non-toxic organic solvents, such as paraffins (for example mineral oil fractions), vegetable oils (for example ground nut oil/sesame oil), alcohols (for example ethyl alcohol and glycerol), excipients, such as, for example, natural rock powders (for example kaolins, clays, talc and chalk), synthetic rock powders (for example highly disperse silica and silicates), sugars (for example sucrose, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in a customary manner, preferably orally or parenterally, in particular perlingually or intravenously. In the case of ora use, tablets can, of course, also contain, in addition to the excipients mentioned, additives such as sodium citrate, calcium carbonate and dicalcium phosphate, together with various additional substances, such as starch, preferably potato starch, gelatin and the like. Furthermore, lubricants, such as magnesium stearate, sodium lauryl sulphate and talc, can also be used when making tablets. In the case of aqueous suspensions, the active compounds can be mixed with various flavor-improving agents or colorants in addition to the abovementioned auxiliary substances.

In the case of parenteral use, solutions of the active compounds, employing suitable liquid excipients, can be used.

In general, it has proved advantageous, in the case of intravenous administration, to administer amounts of about 0.001 to 1 mg/kg, preferably about 0.01 to 0.5 mg/kg, of body weight to achieve effective results, and in the case of oral administration, the dosage is about 0.01 to 20 mg/kg, preferably 0.1 to 10 mg/kg, of body weight.

Nevertheless, it can at times be necessary to deviate from the amounts mentioned, and in particular to do so as a function of the body weight of the experimental animal or of the nature of the administration method, the animal's individual behavior towards the medicament, and the nature of the formulation of the medicament and the time or interval at which the administration takes place. Thus it can suffice in some cases to manage with less than the abovementioned minimum amount, whilst in other cases the upper limit mentioned must be exceeded. Where relatively large amounts are administered, it can be advisable to divide these into several individual administrations over the course of the day.

PREPARATION EXAMPLES

Example 1

Diethyl 3-acetyl-2-(2-ethoxyphenyl)-6-hydroxy-4-phenylcyclohex-6-ene,1,3-dicarboxylate

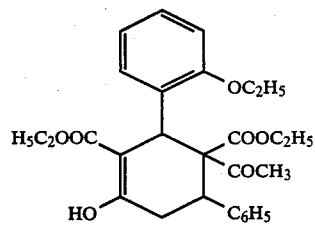

1 ml of a 1% sodium ethanolate/ethanol solution and a solution of 2.2 g (0.01 mol) of ethyl 3-oxo-5-phenyl-4-pentenoate in 10 ml of ethanol a solution of 2.6 g (0.01 mol) of ethyl 2-acetyl-3-(2-ethoxyphenyl)-propenoate in 20 ml of ethanol and the mixture is stirred at room temperature for 1 day. It is then filtered with suction and the residue is washed with ethanol.

Yield: 2.9 g (60.3% of theory).

Melting point: 162° C.

Example 2

Ethyl 3-cyano-6-hydroxy-3-methylsulphonyl-2-(2-nitrophenyl)-4-phenyl-cyclohex-6-ene-1-carboxylate

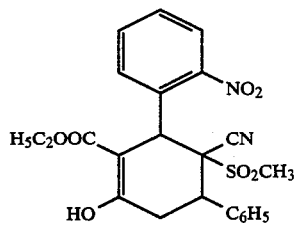

A mixture of 2.2 g (0.01 mol) of ethyl 3-oxo-5-phenyl-4-pentenoate, 2.5 g (0.01 mol) of 1-methylsulphonyl-2-(2-nitrophenyl)-acrylonitrile and 1.1 ml of concentrated ammonia in 15 ml of ethanol is stirred for 2 days at room temperature. It is then filtered with suction and the residue is washed with ethanol.

Yield: 2.7 g (57.3% of theory).

Melting point: 180° C.

The compounds listed in the table below were synthesized analogously to Examples 1 and 2:

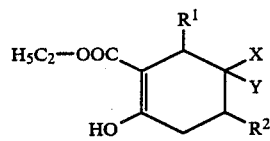
| EXAMPLE No. | R¹ | R² | X | Y | MELTING POINT [°C.] | YIELD [% THEORY] |
|---|---|---|---|---|---|---|
| 3 | (phenyl) | $C_6H_5$ | CN | CN | 187 | 88.7 |
| 4 | (phenyl) | $C_6H_5$ | $COOC_2H_5$ | CN | 128 | 83.4 |
| 5 | (2-CF₃-phenyl) | $C_6H_5$ | $COOC_2H_5$ | CN | 124 | 65.8 |
| 6 | (2-Cl-phenyl) | $C_6H_5$ | $COOC_2H_5$ | CN | 161 | 46.3 |
| 7 | (3-NO₂-phenyl) | $C_6H_5$ | $COOC_2H_5$ | CN | 134 | 43.1 |
| 8 | (2-NO₂-phenyl) | $C_6H_5$ | $COOC_2H_5$ | CN | 206 | 90.5 |
| 9 | (2,4-di-Cl-phenyl) | $C_6H_5$ | $COOC_2H_5$ | CN | 136 | 59.0 |
| 10 | (2-CF₃-phenyl) | $C_6H_5$ | $SO_2CH_3$ | CN | 201 | 28.4 |
| 11 | (2,6-di-Cl-phenyl) | $C_6H_5$ | $COOCH_3$ | CN | 125 | 52.7 |
| 12 | (2-CF₃-phenyl) | $C_6H_5$ | $COOC_2H_5$ | $COOC_2H_5$ | 102 | 20.6 |

-continued
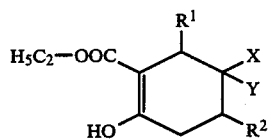
| EXAMPLE No. | R¹ | R² | X | Y | MELTING POINT [°C.] | YIELD [% THEORY] |
|---|---|---|---|---|---|---|
| 13 | 4-OCH₃-C₆H₄ | C₆H₅ | COOC₂H₅ | CN | 157 | 15.6 |
| 14 | 4-CH₃-C₆H₄ | C₆H₅ | COOC₂H₅ | CN | 184 | 69.3 |
| 15 | 4-NO₂-C₆H₄ | C₆H₅ | COOC₂H₅ | CN | 182 | 73.3 |
| 16 | 3-NO₂-C₆H₄ | C₆H₅ | COOC₂H₅ | COOC₂H₅ | 116 | 45.0 |
| 17 | 2-Cl-C₆H₄ | C₆H₅ | SO₂CH₃ | CN | 179 | 65.3 |
| 18 | 2-Cl-C₆H₄ | C₆H₅ | COOC₂H₅ | COCH₃ | 132 | 74.5 |
| 19 | 3-NO₂-C₆H₄ | CH₃ | COOC₂H₅ | COOC₂H₅ | 105 | 22.3 |
| 20 | 2-NO₂-C₆H₄ | C₆H₅ | COOC₂H₅ | COOC₂H₅ | 149 | 15.7 |
| 21 | 2-CF₃-C₆H₄ | C₆H₅ | COOC₂H₅ | COCH₃ | 144 | 19.8 |

-continued

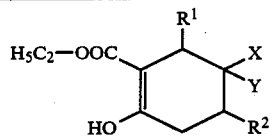

| EXAMPLE No. | R¹ | R² | X | Y | MELTING POINT [°C.] | YIELD [% THEORY] |
|---|---|---|---|---|---|---|
| 22 | (2,3-dichlorophenyl) | $C_6H_5$ | $COOC_2H_5$ | $COCH_3$ | 120 | 19.5 |
| 23 | (4-nitrophenyl) | $CH_3$ | $COOC_2H_5$ | CN | 102 | 19.9 |
| 24 | 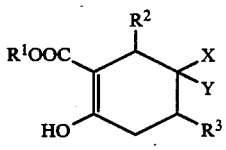 | $C_6H_5$ | $COOC_2H_5$ | $COCH_3$ | 178 | 25.7 |

It will be appreciated that the instant specification and claims are set forth by way of illustration and not limitation, and that various modifications and changes may be made without departing from the spirit and scope of the of the present invention.

We claim:

1. A cyclohexenecarboxylate of the formula $$\text{(I)}$$

in which $R^1$ represents a straight-chain or branched saturated or unsaturated hydrocarbon radical with up to 20 carbon atoms, which is optionally interrupted by an oxygen atom or a sulphur atom in the chain, or a cyclic hydrocarbon radical with up to 20 carbon atoms, which straight-chain or branched or cyclic hydrocarbon is optionally substituted by halogen, cyano, hydroxyl, acetyloxy, nitro, nitrooxy or by a phenyl, phenoxy, phenylthio or phenylsulphonyl group which is optionally substituted by halogen, cyano, dialkylamino with in each case 1 to 2 carbon atoms to each alkyl group, alkoxy with 1 to 4 carbon atoms, alkyl with 1 to 4 carbon atoms, trifluoromethyl or nitro, or by an amino group, where this amino group carries 2 identical or different substituents from the group alkyl with up to 4 carbon atoms, alkoxyalkyl with up to 4 carbon atoms, phenyl or $C_7$–$C_{14}$-aralkyl, or an N-phenyl or N-alkyl grouping, where this alkyl group is 1 to 3 carbon atoms, $R^2$ represents $C_6$–$C_{12}$-aryl, which can be mono-, di- or trisubstituted by halogen, $C_1$–$C_8$-alkyl, $C_1$–$C_8$-alkoxy, $C_1$–$C_6$-alkylthio, $C_1$–$C_6$-alkylsulphonyl, trifluoromethyl, trifluoromethoxy, difluoromethoxy, trifluoromethylthio, nitro, cyano, $C_1$–$C_4$-alkoxycarbonyl, di-$C_1$–$C_6$-alkylamino, dimethylaminosulphonyl or dimethylcarbamoyl, the substituents being identical or different, $R^3$ represents $C_1$–$C_6$-alkyl or represents $C_6$–$C_{12}$-aryl, which can be mono- or disubstituted by halogen, $C_1$–$C_4$-alkyl, $C_1$–$C_4$-alkoxy, cyano, trifluoromethyl or trifluoromethoxy, the substituents being identical or different, and X and Y are identical or different and represent a group of the formula —CN, —COR⁴, —SO₂R⁴, —COOR⁵, —CONR⁶R⁷ or —SO₂NR⁶R⁷, wherein $R^4$ denotes $C_1$–$C_8$-alkyl, $C_6$–$C_{12}$-aryl or $C_7C_{14}$-aralkyl, $R^5$ denotes $C_1$–$C_8$-alkyl or $C_6$–$C_{12}$-aryl, and $R^6$ and $R^7$ are identical or different and denote $C_1$–$C_6$-alkyl, $C_6$–$C_{12}$-aryl or $C_7$–$C_{14}$-aralkyl, with the proviso that at least one of X and Y is —CN or —COOR⁵.

2. A compound according to claim 1, in which $R^1$ represents a straight-chain or branched saturated or unsaturated hydrocarbon radical with up to 14 carbon atoms, which is optionally interrupted by an oxygen atom in the chain, or a cyclic hydrocarbon radical with up to 14 carbon atoms, which straight-chain or branched or cyclic hydrocarbon is optionally substituted by fluorine, chlorine, bromine, iodine, cyano, hydroxyl, acetoxy, nitrooxy or by a phenyl or phenoxy group which is optionally substituted by fluorine, chlorine, bromine, alkoxy with 1 to 4 carbon atoms, alkyl with 1 to 4 carbon atoms or trifluoromethyl, or by an amino group, where this amino group carries 2 identical or different substituents from the group alkyl with 1 to 4 carbon atoms, phenyl or benzyl, $R^2$ represents phenyl or naphthyl, where the radicals mentioned can be mono- or disubstituted by fluorine, chlorine, bromine, $C_1-C_6$-alkyl, $C_1-C_6$-alkoxy, $C_1-C_4$-alkylthio, $C_1-C_4$-alkylsulphonyl, trifluoromethyl, trifluoromethoxy, difluoromethoxy, nitro, cyano, $C_1-C_4$-alkoxycarbonyl or di-$C_1-C_4$-alkylamino, the substituents being identical or different, $R^3$ represents $C_1-C_4$-alkyl or represents phenyl or naphthyl, where the radicals mentioned can be substituted by fluorine, chlorine, methyl, methoxy or trifluoromethyl, and $R^4$ denotes $C_1-C_6$-alkyl, phenyl or benzyl, $R^5$ denotes $C_1-C_6$-alkyl or phenyl, and $R^6$ and $R^7$ are identical or different and denote $C_1-C_4$-alkyl, phenyl or benzyl, with the proviso that at least one of X and Y is —CN or —COOR$^5$.

3. A compound according to claim 1, in which $R^1$ represents a straight-chain or branched hydrocarbon radical with up to 8 carbon atoms, which is optionally interrupted by an oxygen atom in the chain, or a cyclic hydrocarbon radical with up to 14 carbon atoms, which straight-chain or branched or cyclic hydrocarbon is optionally substituted by fluorine, cyano, acetoxy, hydroxyl, phenyl, phenoxy, or an amino group, where this amino group carries two identical or different substituents from the group alkyl with 1 to 2 carbon atoms and benzyl, $R^2$ represents phenyl, which can be mono- or disubstituted by fluorine, chlorine, $C_1-C_4$-alkyl, $C_1-C_4$-alkoxy, trifluoromethyl or nitro, the substituents being identical or different, $R^3$ represents methyl or phenyl, and X and Y are identical or different and represent a group of the formula —CN, —COR$^4$, —SO$_2$R$^4$ or —COOR$^5$, wherein $R^4$ denotes $C_1-C_4$-alkyl, phenyl or benzyl and $R^5$ denotes $C_1-C_4$-alkyl, with the proviso that at least one of X and Y is —CN or —COOR$^5$.

4. A compound according to claim 1, wherein such compound is diethyl 3-acetyl-2-(2-ethoxypheny)-6-hydroxy-4-phenylcyclohex-6-ene-1, 3-dicarboxylate of the formula

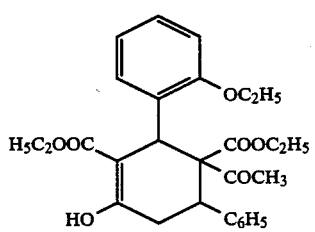

5. A compound according to claim 1, wherein such compound is ethyl 3-cyano-6-hydroxy-3-methylsulphonyl-2-(2-nitrophenyl)-4-phenyl-cyclohex-6-ene-1-carboxylate of the formula

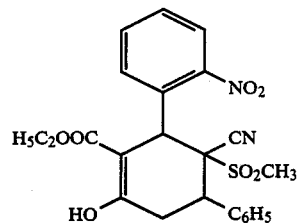

6. A compound according to claim 1, wherein such compound is ethyl 3,3-dicyano-2,4-diphenyl-6-hydroxy-cyclohex-6-ene-carboxylate of the formula

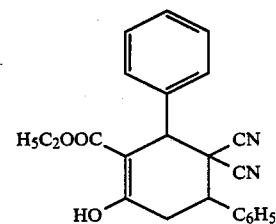

7. A compound according to claim 1, wherein such compound is diethyl 3-cyano-2-(2-trifluoromethylphenyl)-6-hydroxy-4-phenyl-cyclohex-6-ene-1,3-dicarboxylate of the formula

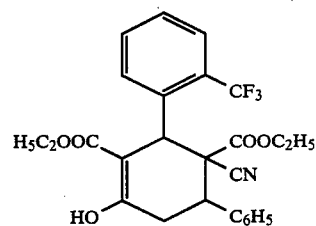

8. A compound according to claim 1, wherein such compound is triethyl 2-(2-trifluoromethylphenyl)-4-phenyl-6-hydroxycyclohex-6-ene-1,3,3-tricarboxylate of the formula

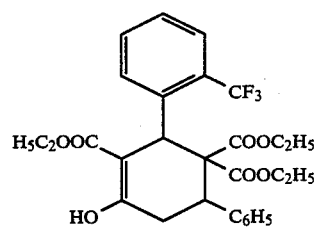

9. A compound according to claim 1, wherein such compound is triethyl 2-(3-nitrophenyl)-4-phenyl-6-hydroxy-cyclohex-6-ene-1,3,3-tricarboxylate of the formula

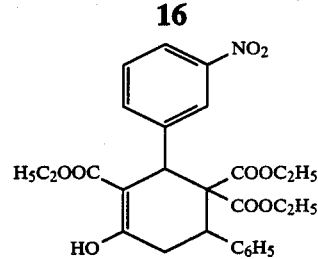

10. A circulation-active composition comprising an amount effective therefor of a compound according to claim 1 and a diluent.

11. A unit dose of a composition according to claim 10 in the form of a pill, capsule or ampule.

12. A method of normalizing the circulation of a patient in need thereof which comprises administering to such patient an amount effective therefor of a compound according to claim 1.

* * * * *